United States Patent [19]

Sanderson

[11] 4,129,588

[45] Dec. 12, 1978

[54] SELECTIVE MANUFACTURE OF ANHYDROUS MODIFICATIONS OF METHYL PHOSPHONIC ACID AND USE THEREOF IN MAKING PURE METHYL PHOSPHONIC ACID AND SALTS THEREOF

[75] Inventor: William A. Sanderson, Palo Alto, Calif.

[73] Assignee: The United States of America as represented by the Secretary of Agriculture, Washington, D.C.

[21] Appl. No.: 394,982

[22] Filed: Sep. 7, 1973

[51] Int. Cl.$^2$ ................................................ C07F 9/38
[52] U.S. Cl. ........................ 260/502.4 P; 260/502.4 R
[58] Field of Search ..................... 260/502.4 P, 502.4 R

[56] References Cited

U.S. PATENT DOCUMENTS

| | | | |
|---|---|---|---|
| 2,304,157 | 12/1942 | Englemann et al. | 260/502.5 |
| 2,951,863 | 9/1960 | Dawson et al. | 260/986 |
| 3,400,149 | 9/1968 | Quimby et al. | 260/502.4 P |
| 3,600,435 | 8/1971 | Randall et al. | 260/502.4 P |

OTHER PUBLICATIONS

Kosolapuff, "Organophosphorus Compounds", 1950, p. 148.

*Primary Examiner*—Joseph E. Evans
*Attorney, Agent, or Firm*—M. Howard Silverstein; David G. McConnell

[57] ABSTRACT

Pyro-methyl phosphonic acid (methyl phosphonic acid monoanhydride) is obtained in a high degree of purity and a yield approaching 100% of theory by the pyrolysis of dimethyl hydrogen phosphite in liquid phase. The pyrolysis product is then converted to methyl phosphonic acid by boiling with water. If desired, the resulting aqueous acid solution may be directly converted to a salt, e.g., to monoammonium methyl phosphonate by the addition of one mole of ammonia per mole of methyl phosphonic acid, or water may be evaporated from the aqueous acid solution and crystalline methyl phosphonic acid may thus be recovered.

7 Claims, No Drawings

SELECTIVE MANUFACTURE OF ANHYDROUS MODIFICATIONS OF METHYL PHOSPHONIC ACID AND USE THEREOF IN MAKING PURE METHYL PHOSPHONIC ACID AND SALTS THEREOF

BACKGROUND OF THE INVENTION

Pyro-methyl phosphonic acid (pyro-MPA) is useful as an intermediate in the manufacture of various organophosphorus compounds which are useful as flame retardants or for other purposes. More particularly, pyro-MPA is a useful precursor in the manufacture of methyl phosphonic acid (MPA), a compound having the formula

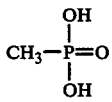

which is useful as a flame retardant or as a component of flame retardant systems for fabrics. For instance, MPA may be applied to fabrics as a flame retardant finish in the form of an aqueous solution of its ammonium salt in combination with cyanamide.

Various methods have been previously proposed for making pyro-MPA from dimethyl hydrogen phosphite (DMP), but such methods have generally been relatively unsatisfactory, producing the desired products in relatively low degrees of purity or low yields and often requiring cumbersome manufacturing procedures. For instance, Dawson et al, in U.S. Pat. No. 2,951,863 refer to the slow rate at which DMP, when heated, is converted to a mixture comprising the methyl ester of MPA and pyro-MPA and describe the difficulties encountered when attempts were made to increase the conversion rate by conducting the reaction in various high boiling heat transfer media. More particularly, Dawson et al, report that no conversion whatever of DMP was obtained after three hours of heating when diphenyl ether was used as a heat transfer medium, and that a hard, glassy, brown solid of no apparent use was obtained as the chief reaction product when an attempt was made to pyrolyze DMP using benzophenone as a heat transfer medium. According to Dawson et al, improved results are obtained if a heavy paraffin oil is used as the heat transfer medium but even in such a system the product of the pyrolysis is reported to contain more than 10% methyl ester of MPA and less than 90% pyro-MPA. As the methyl ester is known to be relatively difficult to hydrolyze in the absence of a strong acid and the use of a high boiling reaction medium necessarily further complicates product recovery, the process described by Dawson et al, still leaves much to be desired as a route for the production of substantially pure MPA.

In U.S. Pat. No. 2,923,729, Hardy describes another process for producing a mixture of methyl ester of MPA and pyro-MPA by the pyrolysis of DMP. This process does not rely on the addition of any extraneous solvent, but requires the continuous circulation of a liquid stream between a primary and a secondary reaction zone such that DMP is fed into and partially pyrolyzed in the circulating liquid in the primary zone and its pyrolysis is "completed" in the secondary zone. Thereupon a portion of the pyrolyzed mixture is recovered from the secondary zone as product and another portion returned to the primary zone. According to this procedure, the heating of the liquid mixture in the secondary zone is continued until the DMP has been substantially completely converted to other compounds, principally methyl ester of MPA and pyro-MPA, i.e., until DMP constitutes less than 2% and preferably less than 0.2% of the liquid pyrolysis product. However, as the pyrolysis in such a case is continued only until the DMP concentration in the reaction mixture approaches or reaches zero, it is evident that the product from the Hardy process is essentially the same kind of mixture as in the Dawson et al, process described above, i.e., a mixture comprising a major proportion of pyro-MPA, a minor but substantial proportion of methyl ester of MPA and usually at least a trace of DMP. As in the case of the Dawson et al process, the product is not one that lends itself to be easily hydrolyzed to form MPA nor one from which pure MPA can be readily recovered in high yields.

Other patent references representative of the prior art relating to the pyrolysis of DMP or similar phosphorus compounds and the production of various phosphonic and phosphinic acids or their anhydrides include the following: U.S. Pat. Nos. 2,268,157 Marvel; 2,365,466 Hamilton; 2,397,422 Kosolapoff; 2,559,754 Bittles, Jr., et al; 2,587,340 Berkeley et al; 2,717,906 Lecher et al; 2,853,515 Coates et al; 2,863,900 Beach et al; 2,929,843 Dawson et al; 3,054,821 Rolih et al; 3,089,889 Cleveland et al; 3,093,673 Beach et al; 3,179,695 Weilmuenster et al; 3,708,535 Firestone; British Pat. No. 734,187 (published July 27, 1955); German DOS No. 2,007,784 (published Oct. 15, 1970).

References in the general chemical literature which have been considered include "Synthesis and Properties of Phosphinic and Phosphonic Acid Anhydrides" by Moedritzer, *J. Am. Chem. Soc.*, Vol. 83, p. 4381 (1961); "Addition Reactions of the Phosphorus Halides V. The Formation of an Unsaturated Phosphonic Acid" by Conant and Coyne, *J. Am. Chem. Soc.*, Vol. 44, p. 2530 (1922); "Trichloromethylphosphonic Acid" by Bengelsdorf and Barron, *J. Am. Chem. Soc.*, Vol. 71, p. 2869 (1955); *Chemical Abstracts* 2685–2687, Vol. 47 (Yakubovich et al); *Bull. Soc. Chim.*, France (1961), 1084 (Monard and Quinchon) DMP Used as Route to MeP(O)Cl$_2$ By Treatment of the Pyrolyzed Product With SOCl$_2$ or PCl$_5$; and *Memorial des Poudres*, 44, 119–32 (1962) (Quinchon et al), Action of SOCl$_2$ on Products Produced by the Pyrolysis of Dimethyl Phosphite.

OBJECTS AND SUMMARY OF THE INVENTION

It is a general object of the present invention to provide an improved, more efficient or simpler process for making alkane phosphonic acids in an anhydride form which is substantially free of esters and which can be readily converted to substantially pure free acid by heating with water.

A more particular object is to provide a process for pyrolyzing DMP and thereby making an MPA anhydride which is substantially free of any ester, which can be readily converted to MPA by boiling with water in the absence of any extraneous acid or base catalyst, which does not entail any problems of disposal of halogenated by-products, and which produces MPA in a high degree of purity (preferably higher than 97%) and in a yield higher than 95%, preferably higher than 98%, of theory based on the DMP feed material.

Another object is to provide a two-step process for making aqueous solutions of MPA by pyrolyzing DMP and then directly converting the resulting anhydride-containing pyrolysis product to an aqueous MPA solution by addition of water to the product.

A further object is to provide an efficient process for making substantially pure crystalline MPA by pyrolyzing DMP, converting the resulting pyrolysis product substantially completely to MPA by boiling it in water, and evaporating excess water.

Still another object is to provide an efficient process for making water soluble salts of MPA such as monoammonium methyl phosphonate by pyrolyzing DMP, converting the resulting anhydride-containing product substantially completely to MPA by reaction with water, and adding an appropriate proportion of ammonia or other selected base to the aqueous MPA solution.

These and other objects, the novel ways of achieving them, and the advantages thereof will become more fully apparent from the description which follows.

In pursuit of these objects it has now been discovered that DMP can be readily converted to a product consisting essentially only of pyro-MPA or MPA anhydride when DMP is pyrolyzed, e.g., by heating under reflux, until all of the DMP as well as essentially all of the methyl ester of MPA, which results from the isomerization of DMP in the early stages of the pyrolytic treatment, are converted to a product consisting essentially of pyro-MPA (i.e., the monoanhydride of MPA), and not more than about 3%, preferably less than about 1% of other compounds, such as MPA dianhydride which may be formed in small amounts in the process or ester material which may remain incompletely converted. Dimethyl ether, which is formed as a by-product when DMP is converted to pyro-MPA, is removed from the reaction zone in any appropriate manner, e.g., by passing an inert gas such as nitrogen or carbon dioxide through the reaction zone. The pyro-MPA can then be simply converted to MPA by heating with the required amount of water.

The chemistry involved is known to be complex and all the reactions which take place in the course of the process of the present invention have not been fully determined. However, without intending to be bound by any particular theory or reaction mechanism, it is suggested that the present invention can be envisioned as being essentially based on the following reactions:

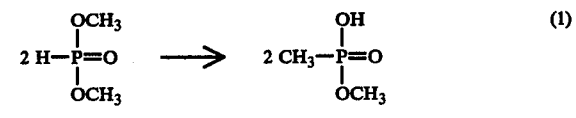

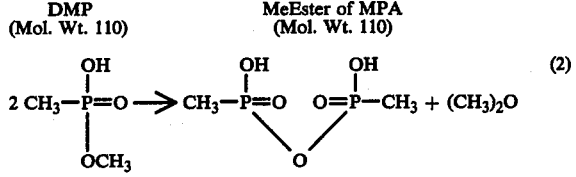

pyro-MPA
(Mol. Wt. 174)

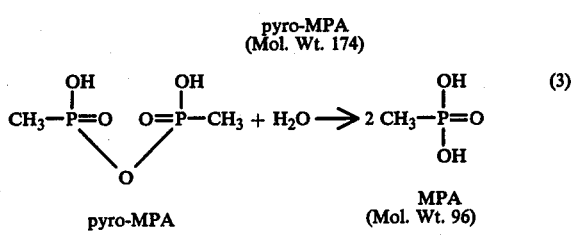

pyro-MPA    MPA
(Mol. Wt. 96)

Referring to the above reactions, when DMP is heated until it substantially disappears from the reaction mixture as suggested by Dawson et al and Hardy, it is first isomerized to give the methyl ester of MPA according to (1) and the methyl ester is then pyrolyzed and condensed to give pyro-MPA and volatile dimethyl ether according to (2), resulting in a liquid mixture consisting essentially of a mixture of pyro-MPA and the unconverted methyl ester. As already stated, the ester in such a mixture is relatively difficult to hydrolyze, requiring the use and ultimate disposal of a strong acid such as hydrochloric acid, and therefore does not represent an attractive source for the production of MPA.

It has now been discovered that when heating of the mixture of pyro-MPA and methyl ester of MPA is continued even after all of the DMP has been converted, the conversion of the MPA methyl ester remaining in the reaction mixture continues until essentially no ester remains. The resulting product consisting essentially only of pyro-MPA can then be readily hydrolyzed without requiring the addition of any catalyst, producing MPA simply by boiling with an appropriate amount of water as indicated in (3). It should be understood that one mole of water is required to hydrolyze one mole of pyro-MPA, but that an excess of water may be used and is often found desirable as further discussed below.

GENERAL DESCRIPTION OF THE INVENTION

The pyrolysis of DMP in liquid phase can be conducted in various ways. For instance, DMP, which is a colorless liquid having a boiling point of about 170° C. at atmospheric pressure, may be placed in a reaction vessel equipped with a reflux condenser and heated under reflux under a slow stream of nitrogen or other inert gas to assist in sweeping out the evolving vapors and protecting the reaction mixture against oxidation. In the course of about 15 hours of heating at atmospheric pressure, the liquid temperature rises from about 170° C. to 200° C. as the DMP becomes isomerized and slowly pyrolyzes. At about 200° C. ebullition begins to increase noticeably as a gas, largely dimethyl ether, is evolved. As this evolution tends to become more vigorous as the temperature is increased above 200° C., the rate of heating may be adjusted to maintain the ebullition at a convenient rate.

The heating is continued until no significant gas evolution is observed, at which point all esters present or formed in the mixture will have been substantially completely converted to pyro-MPA and the temperature of the liquid will usually have reached about 300° C. However, depending on the particular heating arrangement used and product purity desired, a final temperature of 280° C. can be sufficient for achieving the desired conversion, and carrying the heating to a final temperature higher than 300° C., e.g., 325° C., may be advantageous to accelerate the pyrolysis and insure complete conversion of the esters. The pyrolysis product obtained is a pale yellow viscous liquid.

When the entire process is conducted at atmospheric pressure, total heating time may be between about 20 and 30 hours, somewhat depending on the specific heating schedule or regime and other expedients employed.

The required heating time can be shortened, if desired, by adding some partially pyrolyzed reaction mixture or preferably some of the final anhydride product to the DMP starting material, thereby raising the initial boiling point of the reaction mixture such that it can be heated at higher liquid temperatures and thus more rapidly converted in the early stages of the process than when DMP alone is used as the initial charge. Thus, it can be advantageous to add between about 10 and 100 parts of the pyro-MPA per 100 parts of DMP at the start of the process.

Another way of speeding up the process is to conduct the first stage in a closed vessel under a pressure which is sufficient to maintain DMP in liquid phase while it is heated at a temperature between about 190° and 200° C. For instance, DMP may be initially heated in a closed vessel at a pressure between about 2 and about 5 atmospheres or higher for from about ½ to 5 hours, the dimethyl ether containing vapors are vented from the vessel, and heating continued under reflux at atmospheric pressure until gas evolution ceases. Before starting the initial heating in such a closed system, the reactor should be swept with an inert gas such as nitrogen so as to remove air and thus prevent an explosive mixture from developing when dimethyl ether is evolved in the process.

Still another way is to pass the DMP at substantially atmospheric pressure through a heated, elongated tubular reactor, e.g., a packed tube which is heated to between about 190° and 210° C. in its front portion and may be heated to higher temperatures in its intermediate and terminal portions. In such a reactor the DMP is vaporized in the front portion of the tube but subsequently condenses as the higher boiling methyl ester of MPA is formed from DMP by isomerization and the resulting liquid mixture is then pyrolyzed in liquid phase. As in all other modifications of the present invention, the important point in the present invention is not the particular state or temperature at which the pyrolysis is conducted, but rather its extent. Regardless of the particular temperature profile or regime selected, the essential point is to conduct the heating long enough until all ester is substantially fully converted to pyro-MPA.

When the pyrolysis has been carried to the desired extent and all ester has been substantially completely converted, the resulting anhydride product is allowed to cool, e.g., to a temperature below 100° C., and water is added in an amount at least sufficient to hydrolyze the pyro-MPA. The addition of about one volume of water per volume of anhydride product is more than sufficient and a convenient proportion to work with. However, a lesser quantity, sufficient to convert all pyro-MPA to MPA, may be used if it is desired to make a concentrated MPA solution, or two or more volumes of water per volume of anhydride product may be used if one desires to obtain a dilute aqueous MPA solution. Upon addition of water, the solution is heated or boiled until hydrolysis is completed, e.g., it is heated at reflux for 1 hour, after which the reflux condenser can be removed, and excess water may then be evaporated under a fast stream of nitrogen or under reduced pressure. When solid MPA is wanted, heating is continued until the liquid temperature reaches 150° C. and no more water is evolved. The liquid residue is poured into a shallow vessel to cool, forming an almost white, crystalline mass of methyl phosphonic acid. A yield of better than 95% is readily obtained and yields better than 99.5% of theory (based on DMP charged) have been obtained when good practice is followed. In typical cases the product will titrate as 99% pure MPA.

When a perfectly water white product is desired, the aqueous MPA solution may be treated with a small amount of decolorizing charcoal and filtered prior to evaporation and crystallization.

If the desired end product is monoammonium methyl phosphonate, e.g., for use in applying a flame retardant finish to fabrics, the desired quantity of ammonia can be added directly to the aqueous MPA solution upon completion of the hydrolysis.

Unless otherwise indicated, all amounts and proportions of materials are stated on a weight basis throughout this specification and claims.

DESCRIPTION OF SPECIFIC EMBODIMENTS

EXAMPLE 1

4140 parts dimethyl phosphite (purified before use by redistillation at 72°-3° C./24mm.) was heated to reflux under a slow stream of nitrogen. In the course of about 15 hours, the liquid temperature rose from 170° C. to 200° C. At this temperature, ebullition began to increase as a gas (largely dimethyl ether) was evolved. This evolution became more vigorous as the temperature increased, and the rate of heating was adjusted accordingly. The heating was continued until the reaction temperature reached 300° C. and no significant gas evolution was observed. The total heating time was 24 hours. The product, a pale yellow viscous liquid, weighed 3250 parts. (The theoretical yield of pyro-MPA is 3275 parts). A small amount of insoluble oil (a hydrocarbon of unknown origin) floated on the surface of the product at this stage. It was insoluble in water and removed with it subsequently during distillation.

The product was allowed to cool to about 80° C. and an approximately equal volume of water was added. The aqueous solution was heated at reflux for 1 hour after which the condenser was removed and the water evaporated off under a fast stream of nitrogen. Heating was continued until the liquid temperature reached 150° C. and no more water was being evolved. The product was poured into a shallow vessel to cool, forming an almost white, crystalline mass of methyl phosphonic acid, 3598 parts (99.7% yield).

Acid-base titration indicated the product was 99% pure MPA.

If a solution of monoammonium methyl phosphonate is required, 35 parts NH$_4$OH is added to the aqueous MPA solution per 96 parts MPA present in the solution.

EXAMPLE 2

1178 parts dimethyl phosphite was heated under a reflux condenser in a slow stream of dry nitrogen. The initial temperature of the refluxing liquid was 172° C., increasing to 186° C. over 8 hours. Heating was continued overnight, and after a total of 23 hours the material in the reaction vessel showed a temperature of 290° C. A faint odor of DMP was noticed during the heating, indicating that some of this reagent was being lost by volatilization. The product was a pale brown viscous liquid, together with a trace of a mobile liquid with a hydrocarbon-like odor. The total weight of product was 901 parts. The theoretical weight of pyro-MPA would be 932 parts.

The product was allowed to cool and then boiled for 1 hour with an approximately equal volume of water. The mobile liquid remained insoluble. The solution was mixed with about 5 parts of decolorizing charcoal, filtered, and evaporated to give a white crystalline material, 995 parts.

The theoretical yield of MPA would be 1028 parts.

Infra-red analysis of the product showed that it was MPA. Acid-base titration indicated 99% purity.

The above description and examples are illustrative of the invention and of practical ways of carrying it out and using it. However, it is to be understood that the invention is not limited thereto but rather is defined by the appended claims and embraces all the variations and modifications thereof which will occur to those skilled in the art upon reading the foregoing specification.

What is claimed is:

1. Process for the selective manufacture of pyro-methyl phosphonic acid from dimethyl phosphite which comprises introducing dimethyl phosphite into a reaction zone, heating the dimethyl phosphite according to a temperature regime which lies predominantly above 170° C., the heating at least in later stages being conducted at temperatures above 200° C. while maintaining the phosphite in liquid phase, whereby vapors of dimethyl ether are evolved, removing the dimethyl ether containing vapors from the reaction zone, and continuing said heating until gas evolution substantially ceases and a liquid product containing more than about 97% pyro-methyl phosphonic acid is obtained.

2. Process according to claim 1 wherein dimethyl phosphite and higher boiling pyrolysis products thereof are introduced into the reaction zone and wherein the heating is conducted under reflux and continued until a liquid mixture is produced consisting essentially of pyro-methyl phosphonic acid and containing less than 2% methyl ester of methyl phosphonic acid.

3. A process according to claim 1 wherein the heating is conducted under reflux and at liquid temperatures which lie between about 280° C. and 325° C. at least in later stages of the process in making said liquid product.

4. A process according to claim 3 wherein an inert gas is passed through the reaction zone to assist in sweeping out the evolving vapors and protecting the liquid against oxidation.

5. A process for the manufacture of methyl phosphonic acid comprising the steps of claim 3 in further combination with the steps of converting the said liquid product to aqueous methyl phosphonic acid by reacting said liquid product with water in an amount sufficient to hydrolyze the pyro-methyl phosphonic acid and form an aqueous methyl phosphonic acid solution.

6. A process according to claim 5 wherein an aqueous solution of methyl phosphonic acid is obtained and water is evaporated from the aqueous solution, thereby recovering substantially pure crystalline methyl phosphonic acid in a yield of at least 95% of theory, based on the dimethyl phosphite starting material.

7. A process for the manufacture of an aqueous solution of monoammonium methyl phosphonate which comprises the steps of claim 5 in combination with the additional step of adding ammonia to the said aqueous methyl phosphonic acid solution in a proportion of one mole of ammonia per mole of methyl phosphonic acid.

* * * * *